US008445693B2

(12) United States Patent
Casar et al.

(10) Patent No.: US 8,445,693 B2
(45) Date of Patent: *May 21, 2013

(54) CATALYZED CARBONYLATION IN THE SYNTHESIS OF ANGIOTENSIN II ANTAGONISTS

(75) Inventors: Zdenko Casar, Ljubljana (SI); Anton Copar, Ljubljana (SI); Jerome Cluzeau, Ljubljana (SI); Andrej Premrl, Ljubljana (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 0 days.

This patent is subject to a terminal disclaimer.

(21) Appl. No.: 12/933,585

(22) PCT Filed: Mar. 19, 2009

(86) PCT No.: PCT/EP2009/053269
§ 371 (c)(1),
(2), (4) Date: Jan. 11, 2011

(87) PCT Pub. No.: WO2009/115585
PCT Pub. Date: Sep. 24, 2009

(65) Prior Publication Data
US 2011/0098329 A1    Apr. 28, 2011

(30) Foreign Application Priority Data

Mar. 20, 2008 (EP) .................... 08153084
Mar. 20, 2008 (EP) .................... 08153085

(51) Int. Cl.
*C07D 235/08* (2006.01)
(52) U.S. Cl.
USPC .................... 548/305.4

(58) Field of Classification Search
USPC .................... 548/305.4
See application file for complete search history.

(56) References Cited

U.S. PATENT DOCUMENTS
2011/0105539 A1*  5/2011  Copar et al. ............ 514/264.1

FOREIGN PATENT DOCUMENTS

| EP | 0502314 A1 | 9/1992 |
|---|---|---|
| EP | 1719766 A2 | 11/2006 |
| WO | WO 2004/087676 A | 10/2004 |
| WO | WO 2006/044648 A1 | 4/2006 |
| WO | WO 2006/103068 A | 10/2006 |

OTHER PUBLICATIONS

E.J. Corey; Robert Robinson Lecture Retrosynthetic Thinking—Essentials and Examples; Chem. Soc. Rev., 1988, vol. 17, pp. 111-133
Marino A. Campo et al.; Synthesis of Fluoren-9-ones via Palladium-Catalyzed Cyclocarbonylation of o-Halobiaryls; Organic Letters 2000; vol. 2, No. 23; pp. 3675-3677.
Jwanro Hassan et al; Aryl-Aryl Bond Formation One Century After the Discovery of the Ullmann Reaction; Chem. Rev., 2002, vol. 102, pp. 1359-1469.
European Search Report; International Application No. PCT/EP2009/053269, Jun. 4, 2009.

* cited by examiner

Primary Examiner — Laura L. Stockton
(74) Attorney, Agent, or Firm — Arent Fox LLP

(57) ABSTRACT

One embodiment disclosed in the invention is the efficient synthesis of halogenated biaryl starting material via Grignard chemistry and the use thereof. Another embodiment of the invention is the reaction of catalyzed carbonylation of the 3'-(2'-halo-biphenyl-4-ylmethyl)-1,7'-dimethyl-2'-propyl-1H,3'H-[2,5']bibenzoimidazolyl (TLMH) using either gaseous carbon monoxide in a solvent mixture containing water; or formic acid salts optionally together with acetic acid in anhydrous solvent.

17 Claims, No Drawings

CATALYZED CARBONYLATION IN THE SYNTHESIS OF ANGIOTENSIN II ANTAGONISTS

CROSS-REFERENCE TO RELATED APPLICATION

This application is a National Stage entry of International Application No. PCT/EP2009/053269, filed Mar. 19, 2009, and published as WO 2009/115585 on Sep. 24, 2009, and claiming priority to EP Application No. 08153085.9 filed Mar. 20, 2008 and EP Application No. 08153084.2 filed Mar. 20, 2008.

FIELD OF THE INVENTION

The present invention relates in general to the field of organic chemistry and in particular to the synthesis of halogenated biaryl starting material via Grignard chemistry and the use thereof. The invention further relates to catalyzed carbonylation of the 3'-(2'-halo-biphenyl-4-ylmethyl)-1,7'-dimethyl-2'-propyl-1H,3'H-[2,5]bibenzoimidazolyl, in particular to use of the said process in preparation of angiotensin II antagonists.

BACKGROUND OF THE INVENTION

Angiotensin II antagonists ("sartans") are efficient active compounds with biological activity which has proved useful for the treatment of hypertension. Most of commercially available sartans contain biphenyl moiety substituted with 5-tetrazolyl or carboxy group on the position 2' (Formula 1, X is COOH or 5-tetrazolyl).

Formula 1

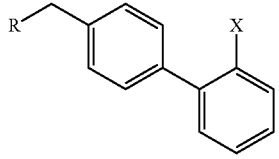

R = sartan specific core

Telmisartan or salt or ester thereof (TLM, Formula 2) known from EP 502314 and which can be prepared in accordance with this invention is used as a pharmaceutical compound alone or in combination with pharmaceutically acceptable carrier for treatment of hypertension in human or animal and functions as angiotensin II antagonists.

Formula 2

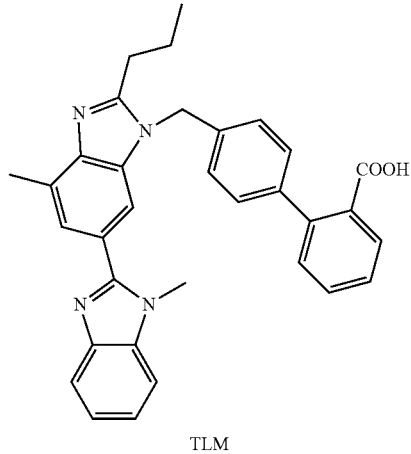

TLM

2'-halo-4-methylbiphenyls (Formula 3, X=Cl, Br, I) are potential starting materials for the synthesis of biphenyl type sartans but they have not found an application in industry due to inefficient or expensive synthesis. Known procedures use Suzuki and Heck couplings which need for industry unfriendly boron and tin compounds, Ullmann reaction (Chem. Rev. 2002, 102, 1359-1469) give low yields and coupling of Grignard intermediates require significant amounts of starting materials (Org. Lett. 2000, 2, 3675-3677). The later reaction was exercised using 1,2-dihalobenzene, 4-halotoluene in the presence of magnesium and iodine for quenching the Grignard intermediate wherein 1,2-dihalobenzene, 4-halotoluene and iodine were used in the ratio of 1:2:3, which is not economically favorable for industrial application.

Formula 3

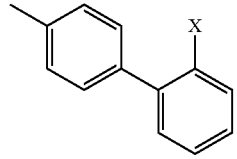

There is a need for efficient synthesis of biphenyl class of sartans especially for carboxy group containing derivatives such as telmisartan.

DISCLOSURE OF THE INVENTION

The object of the present invention is to provide industrially applicable, economical and acceptable process for obtaining telmisartan from cheap starting aromatic compounds. One embodiment disclosed in the invention is the efficient synthesis of halogenated biaryl starting material via Grignard chemistry. A key feature of the invention is a process for preparing telmisartan or salt or ester thereof comprising introducing C-1 synthon on the position 2' of 3'-(2'-halo-biphenyl-4-ylmethyl)-1,7'-dimethyl-2'-propyl-1H,3'H-[2,5]bibenzoimidazolyl. Preferred embodiment of the invention is the reaction of catalyzed carbonylation of the 3'-(2'-halo-biphenyl-4-ylmethyl)-1,7'-dimethyl-2'-propyl-1H,3'H-[2,5]bibenzoimidazolyl (TLMH) using either gaseous carbon monoxide in a solvent mixture containing water; or formic acid salts optionally together with acetic acid in anhydrous solvent.

In a first aspect of the invention is a process for preparing telmisartan or salt or ester thereof, characterized in that TLMH is treated by carbon monoxide, wherein carbon monoxide can be in a gas state or formed in situ from formic acid or its salts. Compounds in the process react in the presence of a catalyst. Catalyst can be selected from transition metal or complex thereof, such as the metal selected from the group consisting of metal palladium, rhodium, nickel, cobalt or iron, or from complex of the said, such as for example the complex with a carbonyl or a phosphine ligand. The aforementioned process is exercised with the reaction set at the temperature of between 20° C. to 180° C. Halo in the 2' position of the biphenyl part is selected from iodo, bromo or chloro.

Particularly the invention is related to the process for obtaining telmisartan, characterized in that TMLH is reacted with carbon monoxide in a mixture of aprotic solvent and water. Reactants can be left to react for 5 to 30 hours, particularly for 10 to 20, more particularly for 12 to 18 hours.

Similarly the invention is related to the process for obtaining telmisartan, characterized in that TMLH is carbonylated using lithium formate and optionally acetic anhydride or acetic anhydride, preferably acetic anhydride. The reactants react in anhydrous solvent. Preferably reactants react for 0.5 to 24 hours, particularly for 2 to 10, more particularly for 4 hours. The temperature at which the reactants react is of between 20° C. to 180° C., particularly at 40° C. to 120° C., more particularly at 80° C.

Another aspect of the invention is use of the process according to any one of the above aspects for preparing telmisartan or salt or ester thereof.

Another aspect of the invention is a process for obtaining a pharmaceutical composition and/or dosage form comprising preparing telmisartan according to the any process disclosed in the above aspects of the invention, and mixing it, optionally in combination with another active pharmaceutical ingredient, with pharmaceutical excipient.

Additional aspect of the present invention is use of the process according to previous aspect for preparing a medicament.

Possible aspect of the invention is also use of a compound selected from 4'-bromomethyl-2-bromo-biphenyl, 4'-iodomethyl-2-iodo-biphenyl, 4'-iodomethyl-2-bromo-biphenyl, 4'-iodomethyl-2-chloro-biphenyl, 4'-chloromethyl-2-iodo-biphenyl, 4'-chloromethyl-2-bromo-biphenyl, or 4'-chloromethyl-2-chloro-biphenyl, wherein said 4'-halomethyl-2-halo-biphenyl is reacted with 2-(1-propyl)-4-methyl-6-(1'-methylbenzimidazole-2-il)benzimidazole, for the synthesis of telmisartan or salt or ester thereof.

DETAILED DESCRIPTION OF THE INVENTION

Surprisingly it has been found that 2'-halo-4-methylbiphenyls can be obtained in a simple one-pot two-step technical process, in yields that are industrially applicable and competitive in which a 4-halotoluene is reacted with a 1,2-dihalobenzene in the presence of elemental metal, wherein less than 1 molar excess of 4-halotoluene in regard to 1,2-dihalobenzene is used, that for each mol of 1,2-dihalobenzene, from 1.0 to 1.9 mol, particularly 1.0 to 1.2 mol 4-halotoluene is used, particularly from 1.05 to 1.15 mol, and arisen organometal intermediates are quenched by elemental halogen. Proportionally for each 1 mol of 1,2-dihalobenzene used in the reaction less than 3 mol, particularly less than 2.9 mol; preferably from 1 to 2 mol, more preferably 1 mol of elemental halogen is used to quench the organometal intermediate.

Scheme 1 represents in first two steps the synthesis of 4'-halomethyl-2-halo-biphenyl.

The present invention provides a process for obtaining 2'-halo-4-methylbiphenyl in which 1 to less than 2 eq. of 4-halotoluene is dissolved in an aprotic solvent, which may be selected from tetrahydrofuran, methyltetrahydrofuran, diethylether, diisopropylether, methyl tertiary butyl ether, dibutyl ether or diphenyl ether and the solution is maintained at about 15° C. to 80° C., preferably at room temperature. 4-halotoluene can be selected from p-bromotoluene, p-chlorotoluene or p-iodotoluene. 2 to 5 eq of metal is added and stirred for about 5 to 180 minutes. By the term metal there is contemplated any embodiment capable of forming organometal intermediates such as, e.g. magnesium, lithium or zinc. To thus prepared mixture one adds 1 eq. of 1,2-dihalobenzene dissolved in the said solvent dropwise at 15° C. to 80° C., preferably at 50 to 60° C. during 1 min to 5 hours, such as during 2 hours and stirred at same temperature for 1 to 48 hours. Dihalobenzene can be selected from 1-bromo-2-chlorobenzene, 1-chloro-2-iodobenzene, 1-bromo-2-iodobenzene, 1,2-dibromobenzene, or 1,2-diiodobenzene. To the solution of thus obtained 4'-methyl-biphenyl-2-ylmetal halide in the said solvent 1 to 5 eq of elemental halogen is added at 15° C. to 80° C., preferably at room temperature. 4'-methyl-biphenyl-2-ylmetal halide can be any appropriate organometal compound such as, e.g. 4'-methyl-biphenyl-2-ylmagnesium halide, wherein halide may be iodide, bromide or chloride, preferably bromide. Elemental halogen is selected from iodine ($I_2$) or bromine ($Br_2$) or chlorine ($Cl_2$). The mixture is stirred for minimum 5 minutes. The remaining halogen is reduced with aqueous solution of $NaHSO_3$ or $Na_2S_2O_3$. After work-up with water and an apolar solvent which may be selected from esters, ethers, chlorinated solvents and hydrocarbons preferably from aliphatic hydrocarbons such as n-hexane, n-pentane, n-heptane, cyclohexane, methylcyclohexane are added. The phases are separated and the organic phase is evaporated. The product is for example purified with LPLC chromatography. Mobile phase is n-hexane, stationary phase is silica gel 60. The fractions are followed by TLC method and collected. The main fractions are evaporated to give 2-halo-4' methyl-biphenyl in yield off at least 60%.

In a more specific but preferred example 1.1 eq of 4-bromotoluene is dissolved in 5 to 7 times bigger volume of tetrahydrofuran and the solution is maintained at room temperature. 2.5 eq of Mg is added and stirred for at least 30 minutes. To thus prepared mixture one adds 1 eq of 1-bromo-2-chlorobenzene diluted by the same volume of tetrahydrofurane dropwise at 55° C. during 2 hours and stirred at same temperature for 1 to 3 hours. To the solution of thus obtained 4'-methyl-biphenyl-2-ylmagnesium bromide in tetrahydrofuran 1 eq of iodine ($I_2$) is added and the reaction is worked up as described above.

The employment of excess of only 0.1 eq of 4-halotoluene dramatically improves the yield, which exceeds in this specific example 60%. Furthermore, only 1 eq of halogen was sufficient to quench the reaction, which lasts 3 hours at most. The procedure is a great improvement of known literature procedures (Org. Lett. 2000, 2, 3675-3677) which takes 14 hours to react and uses over two times excess of 4-halotoluene and three times excess of halogen to achieve comparable yields.

In additional reactions obtained 2-halo-4' methyl-biphenyl is halogenated in dichloromethane yielding 4'-halomethyl-2-halo-biphenyl. Specific compounds thus prepared are 4'-bromomethyl-2-bromo-biphenyl, 4'-iodomethyl-2-iodo-biphenyl, 4'-iodomethyl-2-bromo-biphenyl, 4'-iodomethyl-2-chloro-biphenyl, 4'-chloromethyl-2-iodo-biphenyl, 4'-chloromethyl-2-bromo-biphenyl, 4'-chloromethyl-2-chloro-biphenyl. In one embodiment, said 4'-halomethyl-2-halo-biphenyl can be reacted with 2-(1-propyl)-4-methyl-6-(1'-methylbenzimidazole-2-il)benzimidazole (PMB), to afford TLMH.

In a specific embodiment and as presented in the second part of the Scheme 1 the invention also provides for coupling of 2-halo-4'-bromomethyl-biphenyl and 2-(1-propyl)-4-methyl-6-(1'-methylbenzimidazole-2-il)benzimidazole (PMB), which is performed but not limited as follows: 10-25 mL of sulfolane (tetramethylene sulfone) or N,N-dimethylacetamide or N-methyl-2-pyrrolidone or dimethyl sulfoxide is charged to the flask. 0.85 g of 2-(1-propyl)-4-methyl-6-(1'-methylbenzimidazole-2-yl)benzimidazole and 0.38 g of strong base such as KtBuO or appropriate amount of NaOH, KOH, LiOH, Na$_2$CO$_3$, K$_2$CO$_3$, NaHCO$_3$, KHCO$_3$ are added. The mixture is brought to the temperature of about 25° C.-45° C. to dissolve all the components. The solution is then brought to the temperature of about 5° C. to 25° C. and from 1 to 1.2 equivalents of 2-halo-4'-bromomethyl-biphenyl in 5 to 20 mL of solvent is added during 0.5-5 hours. The reaction mixture is stirred at the same temperature for additional 0-5 hours. 40 mL of demineralised water and 35 mL of ethyl acetate are added. The phases are separated. The EtOAc phase is washed several times with saturated water solution of NaCl. The solvent is evaporated and 4 mL mixture of EtOAc and acetone is added. The suspension is stirred for 15 minutes to 5 hours. The precipitate is filtered off and dried to give TLMH.

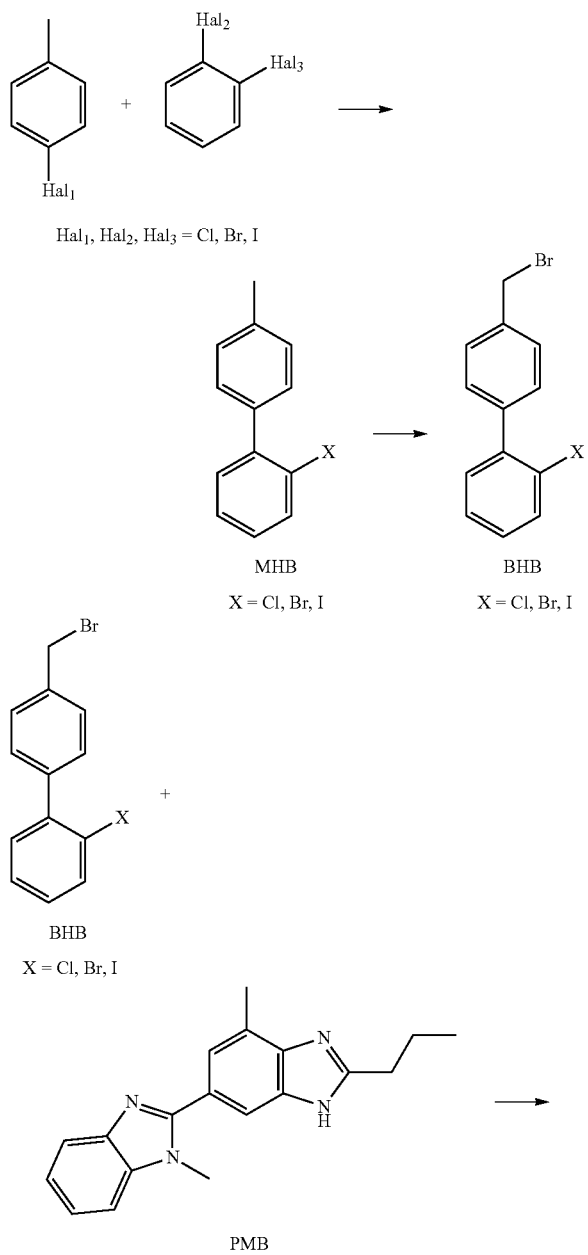

Scheme 1

Hal$_1$, Hal$_2$, Hal$_3$ = Cl, Br, I

MHB
X = Cl, Br, I

BHB
X = Cl, Br, I

BHB
X = Cl, Br, I

PMB

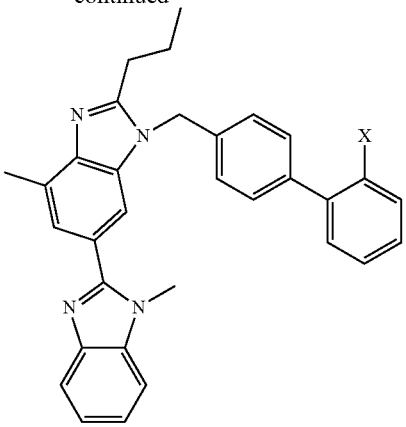

TLMH
X = Cl, Br, I

In accordance with the invention telmisartan is prepared from the intermediate 3'-(2'-halo-biphenyl-4-ylmethyl)-1,7'-dimethyl-2'-propyl-1H,3'H-[2,5]bibenzoimidazolyl (TLMH) by introducing C-1 synthon on the position 2'. Preferably C-1 synthon is introduced in high oxidation state. It can be introduced in one step.

As presented in Scheme 2 telmisartan can be obtained by carbonylation of halo derivative TLMH preferably iodo derivative 3'-(2'-iodo-biphenyl-4-ylmethyl)-1,7'-dimethyl-2'-propyl-1H,3'H-[2,5']bibenzoimidazolyl by reacting with carbon monoxide in the presence of a catalyst, such as transition metals. In one aspect carbon monoxide is used as gas at pressure of 1 to 50 bar, particularly of 1 to 10 bar. In an alternative aspect carbon monoxide is generated in situ by using formic acid and its salts. Transition metals are preferably selected from nickel, cobalt or iron. Preferably they are used in the form of metal carbonyls in the presence of bases selected from hydroxides, hydrides, alkoxides and amines. In addition, the transition metals can be selected from precious metals such as rhodium and palladium, more preferably palladium and preferably in the form of palladium(II) acetate. When using carbon monoxide as gas, the reaction can be performed in a solvent mixture containing water. Preferably the medium of the reaction is a mixture of aprotic solvent and water (wet solvent). Aprotic solvent can be selected from the group comprising tetrahydrofuran, methyltetrahydrofuran, dimethylformamide, toluene, dioxane, diisopropylether, methyl tertiary butyl ether, dibutyl ether, and diphenyl ether. When using carbon monoxide as gas, phosphine ligands are used which can be selected from trialkyl phosphines (R$_3$P), alkylarylphosphines (R$_2$PAr or RPAr$_2$), triarylphosphines (Ar$_3$P) or bis-phosphines (dppe, dppb, dppp, dppf). The reaction temperature is set at between 50° C. to 180° C., preferably at 80° C. to 150° C., particularly at 100° C. In case of using formic acid or its salts, the medium of the reaction is preferably selected from the group comprising aromatic hydrocarbons and amides. Formic acid salts are salts of formic acid and alkali metal, which is for example lithium, sodium or potassium. In particular, the use of lithium formate optionally together in a mixture with acetic anhydride, palladium catalyst with optional addition of base selected from amines in an amide solvent such as N,N-dimethylformamide is most preferred. The reaction temperature when using formic acid salts is set at the temperature of between 20° C. to 180° C., preferably at 40° C. to 120° C., particularly at 80° C.

Scheme 2

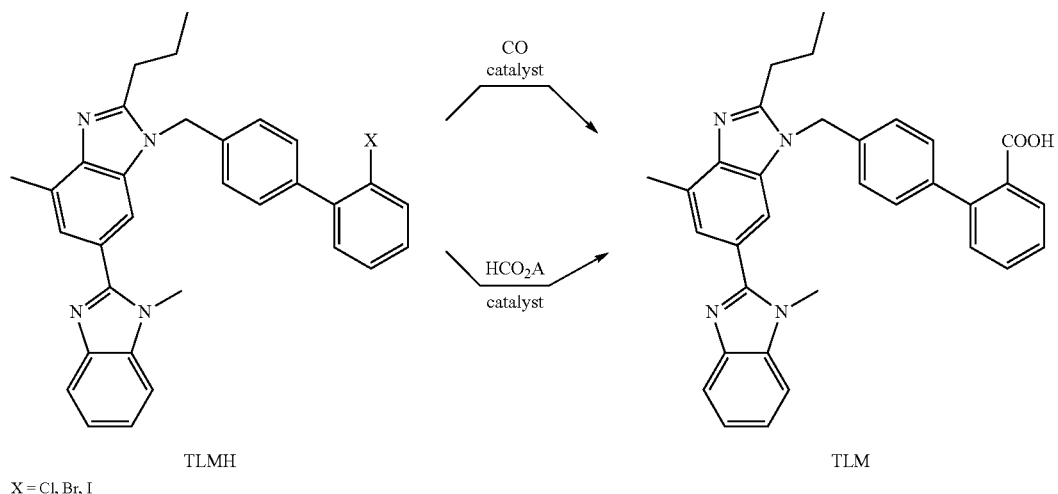

TLMH
X = Cl, Br, I
A = Li, Na, K

TLM

Thus obtained telmisartan or salt or ester thereof can be used for preparing pharmaceutical composition and/or dosage form. The aforementioned process of preparing telmisartan can comprise subsequent steps of mixing said telmisartan, optionally together with another active pharmaceutical ingredient, with pharmaceutical excipient. Suitable pharmaceutical excipients are for example binders (e.g. polyvinylpyrrolidon), disintegrators (e.g. starch, cellulose derivatives), surfactants (e.g. sodium laurylsulphate), pH balancing agents (e.g. citric acid, sodium hydroxide, meglumine), fillers (e.g. mannitol, cellulose derivatives), vehicles (e.g. water, glycerol, alcohol), flavors, colorants (e.g. titanium dioxide). The reason for introducing additional active pharmaceutical ingredient into pharmaceutical composition and/or dosage form together with telmisartan is to achieve synergistic effect of both active pharmaceutical ingredients, or having a goal of addressing two indications simultaneously, or to reduce side effects of the first active pharmaceutical ingredient with the simultaneous or consecutive application of the second active pharmaceutical ingredient, or the like. For example, another active pharmaceutical ingredient can be hydrochlorothiazide, amlodipine or ramipril. The technology used for preparing pharmaceutical formulations and/or dosage forms can be any one known to the person skilled in the pharmaceutical technology. Telmisartan, excipients and optionally another active pharmaceutical ingredient can be simply mixed as powders or dissolved in a suitable solvent. Granulation techniques can be applied to improve the handling properties of said formulation. Dry granulation with compacting or briquetting can be undertaken to prime the granulation mass for tabletting. Similarly, wet granulation with adding or spraying granulation liquid onto particles, powders or already dry granules of compounds can be used to aid formulation of the compounds in the dosage form. Granulation techniques can be used to improve flowability, compressibility, especially when the mass is intended to be used for tabletting. Granulation can also reduce dusting and can determine the dissolution properties. Such properties are desired not only with tablets but also in capsules. It is known, that dosage forms can be in a form of tablets, capsules, pellets, granules, powders, solutions, or the like, wherein solid dosage forms can further be coated or layered. Apparatus such as mixer, tabletting machine, extrudor, granulator can be used in preparing the pharmaceutical composition and/or dosage form. The pharmaceutical composition and/or dosage form can be used for preparing a medicament, meaning that said process of preparing pharmaceutical composition and/or dosage form is expanded to embrace necessary steps for preparing a medicament. Said steps can include determination of the right amount of active pharmaceutical ingredient in the pharmaceutical composition and/or dosage form, packaging, or combining the pharmaceutical composition and/or dosage form with a product leaflet.

The following examples are merely illustrative of the present invention and they should not be considered as limiting the scope of the invention in any way, as these examples and other equivalents thereof will become apparent to those versed in the art in the light of the present disclosure, and the accompanying claims.

Example 1

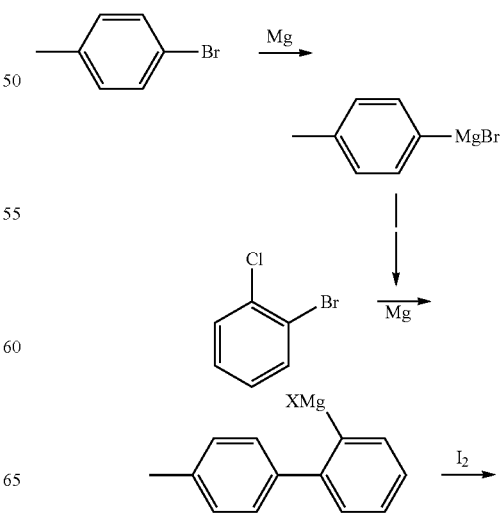

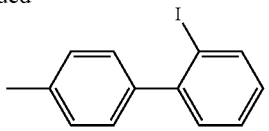

X = Cl, Br

Formation of Grignard Reagent

60 mL of tetrahydrofuran is charged to the flask. 9 g (52.6 mmol) of p-bromotoluene is added and the solution is maintained at 20° C. 3.0 g (125 mmol) of Mg is added and stirred for minimal 30 minutes.

Coupling

9.3 g (48.7 mmol) of 1-bromo-2-chlorobenzene in 5 mL of THF is added into the prepared reaction mixture of p-toluoyl magnesium bromide and remaining magnesium at 55° C. in 2 hours and stirred at 55° C. for 2 hours.

Quenching

The prepared solution of 2-magnesium bromide-4'-methyl-biphenyl is cooled to room temperature, and 20 mL of tetrahydrofuran with further 12.3 g (48.7 mmol) of iodine ($I_2$) are added. The mixture is agitated for minimum 5 minutes. The remaining iodine in neutralised with aqueous solution of $NaHSO_3$. 70 mL of demineralised water and 50 mL of n-hexane are added. The phases are separated and the upper (n-hexane) phase is evaporated. The 15.6 g of yellowish liquid is obtained.

The product is purified with LPLC chromatography. Mobile phase is n-hexane, stationary phase is silicagel 60. The fractions are collected. The main fractions are evaporated. 8.6 g (60%) of 2-iodo-4' methyl-biphenyl (colourless liquid) is obtained.

$^1$H NMR (300 MHz, CDCl$_3$) δ: 2.56 (s, 3H), 7.13 (dt, J=7.5 Hz, J=2.0 Hz, 1H), 7.39 (s, 4H), 7.44 (dd, J=7.6 Hz, J=1.9 Hz, 1H), 7.47-7.52 (m, 1H), 8.09 (dd, J=7.9 Hz, J=1.0 Hz, 1H). $^{13}$C NMR (75 MHz, CDCl$_3$) δ: 146.4, 141.2, 139.3, 137.1, 130.0, 129.0, 128.5, 128.5, 128.0, 98.8, 21.2.

Example 2

Bromination of 2-iodo-4' methyl-biphenyl

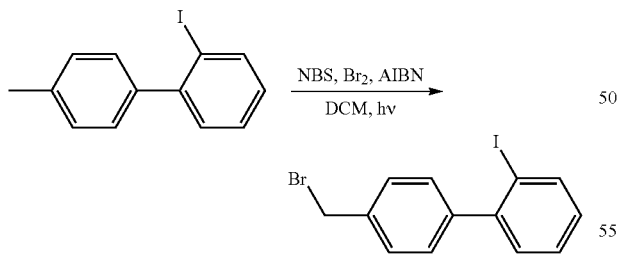

20 mL of dichloromethane (DCM) is charged to the flask. 0.73 g of N-bromosuccinimide (NBS), 0.08 g of 2,2'-azoisobutyronitrile (AIBN), 18 μL of $Br_2$ and 0.9 g of 2-iodo-4'-methyl-biphenyl are added. The reaction is carried out under reflux temperature for minimum 2 hours and the flask is lighted all the time. The reaction is quenched with aqueous solution of $Na_2S_2O_3$. The phases are separated and the lower DCM phase is washed with demineralised water one more time. The DCM phase is evaporated and 4 mL of n-hexane is charged and stirred at room temperature for 30 minutes. The suspension is then cooled to 0° C. and filtered. The cake is washed with 2 mL of solvent. 0.6 g of white crystals of 4'-bromomethyl-2-iodo-biphenyl is obtained.

$^1$H NMR (300 MHz, CDCl$_3$) δ: 4.58 (s, 2H), 7.06 (dt, J=7.6 Hz, J=1.8 Hz, 1H), 7.31 (dd, J=7.7 Hz, J=1.8 Hz, 1H), 7.35 (d, J=8.2 Hz, 2H), 7.40 (dt, J=7.4 Hz, J=1.2 Hz, 1H), 7.48 (d, J=8.2 Hz, 2H), 7.98 (dd, J=7.9 Hz, J=1.1 Hz, 1H). $^{13}$C NMR (75 MHz, CDCl$_3$) δ: 145.8, 144.1, 139.5, 137.0, 130.0, 129.6, 128.9, 128.6, 128.1, 98.3, 33.2.

Example 3

Alkylation of (2-(1-propyl)-4-methyl-6-(1'-methyl-benzimidazole-2-il)benzimidazole)

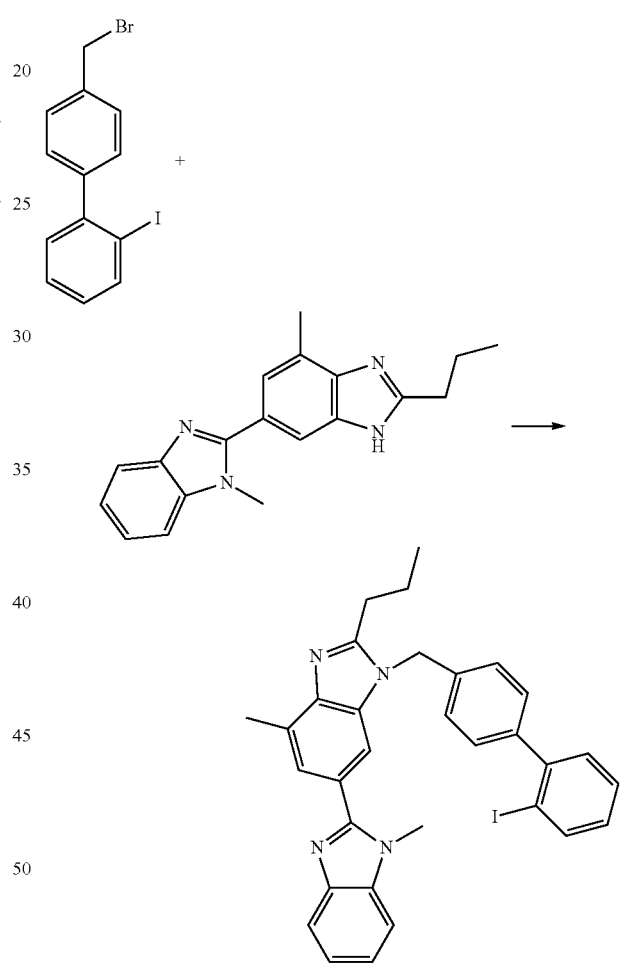

15 mL of sulfolane (tetramethylene sulfone) is charged to the flask. 0.85 g of PMB (2-(1-propyl)-4-methyl-6-(1'-methylbenzimidazole-2-il)benzimidazole) and 0.38 g of potassium tert-butoxide are added. The mixture is heated above 30° C. to dissolve all the components. The solution is than cooled down to 15° C. and 1.07 g of 4'-bromomethyl-2-iodo-biphenyl in 5 mL of solvent is added slowly during 45 minutes. The reaction mixture is stirred at the same temperature for additional 2 hours. 40 mL of demineralised water and 35 mL of EtOAc (ethyl acetate) are added. The phases are separated. The upper EtOAc phase is washed several times with saturated water solution of NaCl. The solvent is evaporated and 4 mL mixture of EtOAc and acetone is added. The suspension is stirred for 30 minutes at room temperature. The suspension is filtered and 0.94 g of white crystals of 3'-(2'-iodo-biphenyl-4-ylmethyl)-1,7'-dimethyl-2'-propyl-1H,3'H-[2,5]bibenzimidazolyl are obtained.

$^1$H NMR (300 MHz, CDCl$_3$) δ: 1.06 (t, J=7.4 Hz, 3H), 1.84-1.92 (m, 2H), 2.95 (t, J=7.8 Hz, 2H), 3.81 (s, 3H), 5.46 (s, 2H), 7.03 (ddd, J=7.9 Hz, J=7.4 Hz, J=1.8 Hz, 1H), 7.13 (d, J=8.0 Hz, 2H), 7.23-7.54 (m, 9H), 7.77-7.83 (m, 1H), 7.94 (dd, J=7.9 Hz, J=1.1 Hz, 1H).

Example 4

Synthesis of telmisartan from 3'-(2'-iodo-biphenyl-4-ylmethyl)-1,7'-dimethyl-2'-propyl-1H,3'H-[2,5]bibenzoimidazolyl by Pd catalyzed hydroxycarbonylation using gaseous carbon monoxide

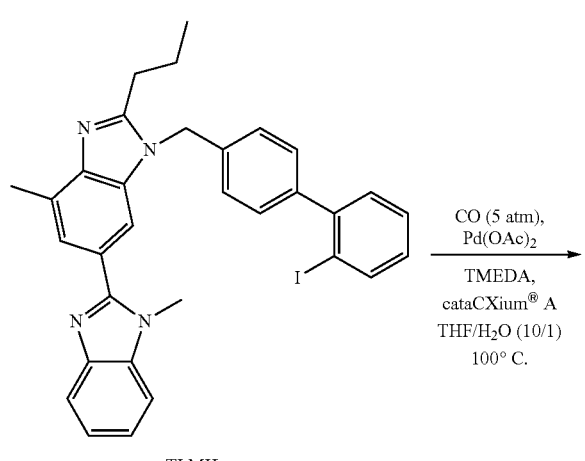

TLMH

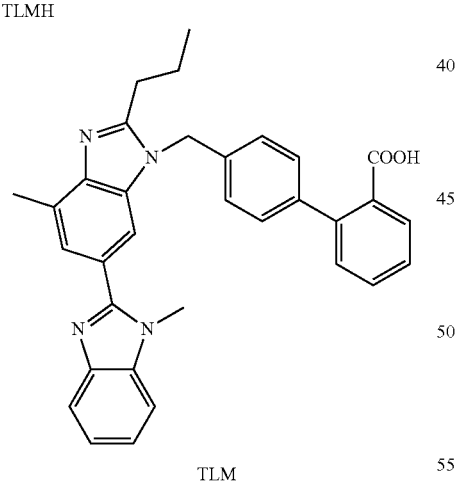

TLM

3'-(2'-iodo-biphenyl-4-ylmethyl)-1,7'-dimethyl-2'-propyl-1H,3'H-[2,5]bibenzoimidazolyl (1 g, 1.68 mmol) was dissolved in 10:1 mixture of tetrahydrofuran (THF) and water (17 mL) and was charged in pressure reactor. Tetramethylethylenediamine (TMEDA; 0.32 mL, 1.25 eq), Pd(OAc)$_2$ (4 mg, 0.01 eq) and cataCXium A® (n-butyldiadamantylphosphine, 18 mg, 0.03 eq) were added. Reactor was flushed three times with carbon monoxide (CO), pressure was adjusted to 5 bar and reactor was heated for 16 h at 100° C. After cooled down to room temperature, the reaction was filtrate on Celite© (diatomaceous earth) and concentrated. Mixture of oily consistency was diluted using NaOH 1N solution and methyl t-butyl ether (MTBE). Phases were separated and organic phase was extracted once again with NaOH 1N solution. Combined aqueous phases were washed twice with MTBE. The pH of the water phase was acidified until pH 3 using 1N HCl and precipitated telmisartan was filtered off. The cake was washed with water. Crude telmisartan (2-[4-[[4-methyl-6-(1-methylbenzoimidazol-2-yl)-2-propyl-benzoimidazol-1-yl]methyl]phenyl]benzoic acid) was obtained.

Example 5

Synthesis of telmisartan from 3'-(2'-iodo-biphenyl-4-ylmethyl)-1,7'-dimethyl-2'-propyl-1H,3'H-[2,5] bibenzoimidazolyl by Pd catalyzed hydroxycarbonylation using lithium formate

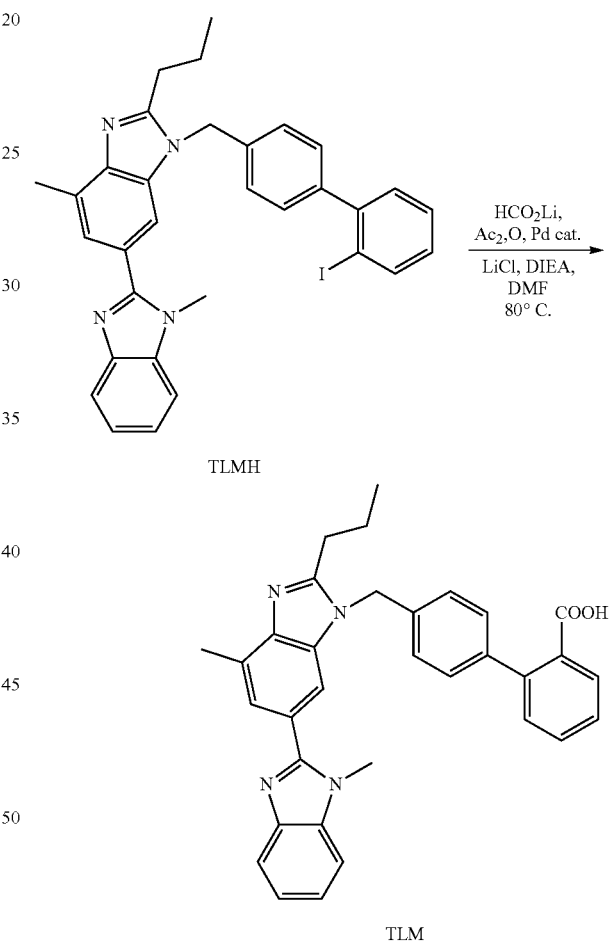

A solution of lithium formate (262 mg, 3 eq), diisopropylethylamine (DIEA; 0.58 mL, 2 eq), acetic anhydride (0.32 mL, 2 eq) in anhydrous dimethylformamide (DMF; 2 mL) was stirred at room temperature for 1 hour. Then, 3'-(2'-iodo-biphenyl-4-ylmethyl)-1,7'-dimethyl-2'-propyl-1H,3'H-[2,5'] bibenzoimidazolyl (1 g, 1.68 mmol), Pd$_2$(dba)$_3$ (38 mg, 0.025 eq, dba is dibenzylideneacetone), LiCl (211 mg, 3 eq) in anhydrous DMF (4 mL) were added. The reaction mixture was stirred at 80° C. for 3 h, filtered and after cooling poured into 1.2 mL of water, stirred for 15 minutes, product filtered, washed with water and dried in vacuo to yield telmisartan.

¹H-NMR (CDCl₃): δ 1.19 (t, 3H, J=7.3 Hz), 2.04 (m, 2H, J=7.6 Hz), 2.76 (s, 3H), 3.27 (t, 2H, J=7.5 Hz), 3.79 (s, 3H), 5.48 (s, 2H), 7.10-8.41 (m, 14H).

(M+H)⁺=515.

The invention claimed is:

1. A process for preparing telmisartan or salt or ester thereof comprising introducing C-1 synthon on the position 2' of 3'-(2'-halo-biphenyl-4-ylmethyl)-1,7'-dimethyl-2'-propyl-1H,3'H-[2,5']bibenzoimidazolyl.

2. A process for preparing telmisartan or salt or ester thereof comprising treating 3'-(2'-halo-biphenyl-4-ylmethyl)-1,7'-dimethyl-2'-propyl-1H,3'H-[2,5']bibenzoimidazolyl with carbon monoxide in the presence of a catalyst.

3. The process according to claim 2, wherein the carbon monoxide is in a gas state or is formed in situ from formic acid or its salts.

4. The process according to claim 2, wherein the catalyst is a transition metal or a complex thereof.

5. The process according to claim 2, wherein the catalyst is selected from the group consisting of metal palladium, rhodium, nickel, cobalt, and iron, complexes thereof with a carbonyl and complexes thereof with a phosphine ligand.

6. The process according to claim 2, wherein the reaction is set at the temperature of between 20° C. to 180° C.

7. The process according to claim 2, wherein the 3'-(2'-halo-biphenyl-4-ylmethyl)-1,7'-dimethyl-2'-propyl-1H,3H-[2,5']bibenzoimidazolyl is reacted with gaseous carbon monoxide in a solvent mixture containing water.

8. The process according to claim 7, wherein the 3'-(2'-halo-biphenyl-4-ylmethyl)-1,7'-dimethyl-2'-propyl-1H,3'H-[2,5']bibenzoimidazolyl and carbon monoxide are left to react for 5 to 30 hours.

9. The process according to claim 2, wherein 3'-(2'-halo-biphenyl-4-ylmethyl)-1,7'-dimethyl-2'-propyl-1H,3H-[2,5'] bibenzoimidazolyl is carbonylated using lithium formate and optionally acetic anhydride.

10. The process according to claim 9, wherein reactants react in anhydrous solvent.

11. The process according to claim 10, wherein reactants react for 0.5 to 24 hours.

12. A process for obtaining a pharmaceutical composition and/or dosage form comprising preparing telmisartan according to claim 1, and mixing it, optionally in combination with another active pharmaceutical ingredient, with a pharmaceutical excipient.

13. The process according to claim 6, wherein the reaction is set at the temperature of between 50° C. to 180° C.

14. The process according to claim 6 wherein the reaction is set at the temperature of between at 80° C. to 150° C.

15. The process according to claim 6, wherein the reaction is set at the temperature of 100° C.

16. The process according to claim 8, wherein the 3'-(2'-halo-biphenyl-4 ylmethyl)-1,7'-dimethyl-2'-propyl-1H,3'H-[2,5']bibenzoimidazolyl and carbon monoxide are left to react 10 to 20 hours.

17. The process according to claim 8, wherein the 3'-(2'-halo-biphenyl-4-ylmethyl)-1,7'-dimethyl-2'-propyl-1H,3'H-[2,5']bibenzoimidazolyl and carbon monoxide are left to react 12 to 18 hours.

* * * * *